(12) United States Patent
Kornel

(10) Patent No.: US 8,486,077 B1  
(45) Date of Patent: Jul. 16, 2013

(54) PERCUTANEOUS POSTEROLATERAL SPINE FUSION

(76) Inventor: Ezriel E. Kornel, Bedford Hills, NY (US)

( * ) Notice: Subject to any disclaimer, the term of this patent is extended or adjusted under 35 U.S.C. 154(b) by 1283 days.

(21) Appl. No.: 11/650,096

(22) Filed: Jan. 5, 2007

Related U.S. Application Data

(60) Provisional application No. 60/756,711, filed on Jan. 5, 2006.

(51) Int. Cl.
    *A61B 17/56* (2006.01)
    *A61B 17/32* (2006.01)

(52) U.S. Cl.
    USPC .............. 606/86 R; 606/79; 606/279; 606/914

(58) Field of Classification Search
    USPC ................ 606/86 R, 79–85, 87, 92, 86 A, 96, 606/105, 279, 914
    See application file for complete search history.

(56) References Cited

U.S. PATENT DOCUMENTS

| | | | | |
|---|---|---|---|---|
| 4,541,423 A | * | 9/1985 | Barber | 606/80 |
| 4,573,448 A | * | 3/1986 | Kambin | 606/170 |
| 5,976,146 A | * | 11/1999 | Ogawa et al. | 606/86 R |
| 6,666,891 B2 | | 12/2003 | Boehm et al. | |
| 8,328,810 B2 | * | 12/2012 | Patel et al. | 606/79 |
| 2004/0220577 A1 | * | 11/2004 | Cragg et al. | 606/80 |
| 2005/0038514 A1 | | 2/2005 | Helm et al. | |
| 2005/0070913 A1 | | 3/2005 | Milbocker et al. | |
| 2005/0187556 A1 | | 8/2005 | Stack et al. | |
| 2005/0203529 A1 | | 9/2005 | Boehm, Jr. et al. | |

* cited by examiner

*Primary Examiner* — Michael T Schaper  
(74) *Attorney, Agent, or Firm* — Andrew S. Langsam; Pryor Cashman LLP

(57) ABSTRACT

A method, tools, and system for performing a percutaneous or minimally invasive spine fusion procedure are provided. A trocar and then dilator are used to create a channel for a hollow and longitudinally slit delivery tube. The method includes inserting a decorticator, such as a rasp, via a delivery tube, decorticating a first region of a first bone associated with a spine, and pushing a bone fusion substance via the delivery tube to the region to fuse the first region with a second region of a second bone associated with the spine. The spine fusion may be a posterolateral fusion and the first region may be a transverse process region of a lumber spine. The bone fusion substance may be pushed using a pusher instrument inserted into the delivery tube, and the delivery tube may be removed while the pusher instrument is held in place to direct the bone fusion substance.

3 Claims, 4 Drawing Sheets

PERCUTANEOUS POSTEROLATERAL SPINE FUSION

RELATED APPLICATIONS

This application claims priority to U.S. Provisional Patent Application Ser. No. 60/756,711, filed Jan. 5, 2006, the disclosure of which is incorporated herein by reference.

FIELD OF THE INVENTION

The present invention relates to the field of minimally invasive and percutaneous surgeries and related procedures, such as posterolateral spine fusion, including lumbar spine fusion at the transverse processes, and to medical instruments for performing the same.

BACKGROUND OF THE INVENTION

Certain types of spine disease caused by painful relative motion of vertebrae of the spine warrant a procedure known as spinal fusion. Such abnormal and painful motion can be caused by proximity of discs, abnormal slippage of the vertebrae and other degenerative spinal conditions. In addition, certain conditions involving instability of the spine, and certain types of fractures, infections, deformities or tumors may also warrant spinal fusion.

Traditionally, an open surgical or invasive technique is used, according to which an incision is generally first made; a portion of a bone is removed or decorticated; a bone fusing substance, such as some combination of allograft bone, autograft bone, including bone marrow aspirant, such as marrow from the iliac crest, morselized bone and/or bone morphogenic protein (BMP) or the like is inserted between the decorticated areas of two vertebra, such as the decorticated area of a transverse process of a vertebra and the decorticated area of a transverse process of an adjacent vertebra (performed on both sides of the spine); thereby to fuse the vertebrae. In addition, pedicle screw fixation using screws bilaterally applied to the pedicles of each vertebral segments and rods may also be used while the bone graft solidifies and becomes stable enough to fuse the vertebrae. Also, three or more vertebrae may thus be fused in the spine fusion procedure by extending the bone graft to the transverse processes of three or more vertebrae.

Recently, certain types of minimally invasive spine procedures have become known. Boehm et al., U.S. Pat. No. 6,666, 891 teaches an interbody spine fusion method, according to which a disk of the spine is removed, and bone matrix is passed through a dilator to encourage fusion at the disc space. Also, Helm et al., US Patent Application Publication Number 2005/0038514 discloses a spine fusion method and system, according to which the disc is removed and fusion is encouraged at the disc cavity. Also known is an X-tube procedure for interbody spinal, fusion in which a disk is removed, and a sextant is used to attach rods and screws. These references and the X-tube procedure however, involve removal of a disk of the spine and are not directed to performing a non-surgical spinal fusion at a transverse process.

Further, Boehm et al., US Patent Application Publication Number 2005/0203529 describes a minimally invasive method for spinal fusion using a bone graft capsule for facilitating the fusion, such that a portion of the transverse processes of vertebrae is cut and a string of capsules strung on a bioabsorbable string is introduced between the transverse processes by means of a device inserted into the body via a separate incision, which device grasps the string. However, this technique requires multiple incisions in the patient's body and requires cumbersome application of the bone matrix or bone fusion substance. Further, these references do not disclose pushing the bone fusion substance via a delivery tube to the decorticated transverse processes or to other areas of interest.

SUMMARY OF THE INVENTION

A method of performing a spine fusion procedure is provided. The method includes inserting a decorticator via a delivery tube; decorticating a first region of a first bone associated with a spine; and pushing a bone fusion substance via the delivery tube to the region to fuse the first region with a second region of a second bone associated with the spine. The spine fusion may be a posterolateral fusion and the first region may be a transverse process region.

In such a procedure, the bone fusion substance may be pushed using a pusher instrument which itself is inserted into the delivery tube. Also, the delivery tube may be removed while the pusher instrument is held in place to direct the bone fusion substance. The decorticator may be a rasp.

Also, the procedure may entail first inserting a dilator before inserting the delivery tube, inserting a trocar before inserting the dilator, and inserting a guide wire before inserting the trocar. The trocar may be part of a cannula.

Further, a system for performing a spine fusion procedure is contemplated. Such a system includes a trocar adapted to be inserted into a body through an incision, a dilator adapted to be inserted over the trocar, a delivery tube adapted to be inserted over the dilator, a decorticator adapted to be inserted into the delivery tube and to decorticate a transverse process region, and a pusher instrument adapted to be inserted into the delivery tube and to push a bone fusion substance via the delivery tube to the region.

The trocar, the dilator, the delivery tube, the decorticator and/or the pusher may be adapted to be malleable or adjustable to the curvature of at least a portion of a human spine, according to the spine curvature of a patient. Alternatively, these instruments could be pre-set to various degrees of curvature, and may thus be distributed in sets of various curvature types.

DETAILED DESCRIPTION OF THE INVENTION

Embodiments of the present invention will now be described with reference to the above-identified figures of the Drawings. However, the Drawings and the description herein of the invention are not intended to limit the scope of the invention. It will be understood that various modifications of the present description of the invention are possible without departing from the spirit of the invention. Also, features or steps described herein may be omitted, additional steps or features may be included, and/or features or steps described herein may be combined in a manner different from the specific combinations recited herein without departing from the spirit of the invention, all as understood by those of skill in the art.

Figure 3:
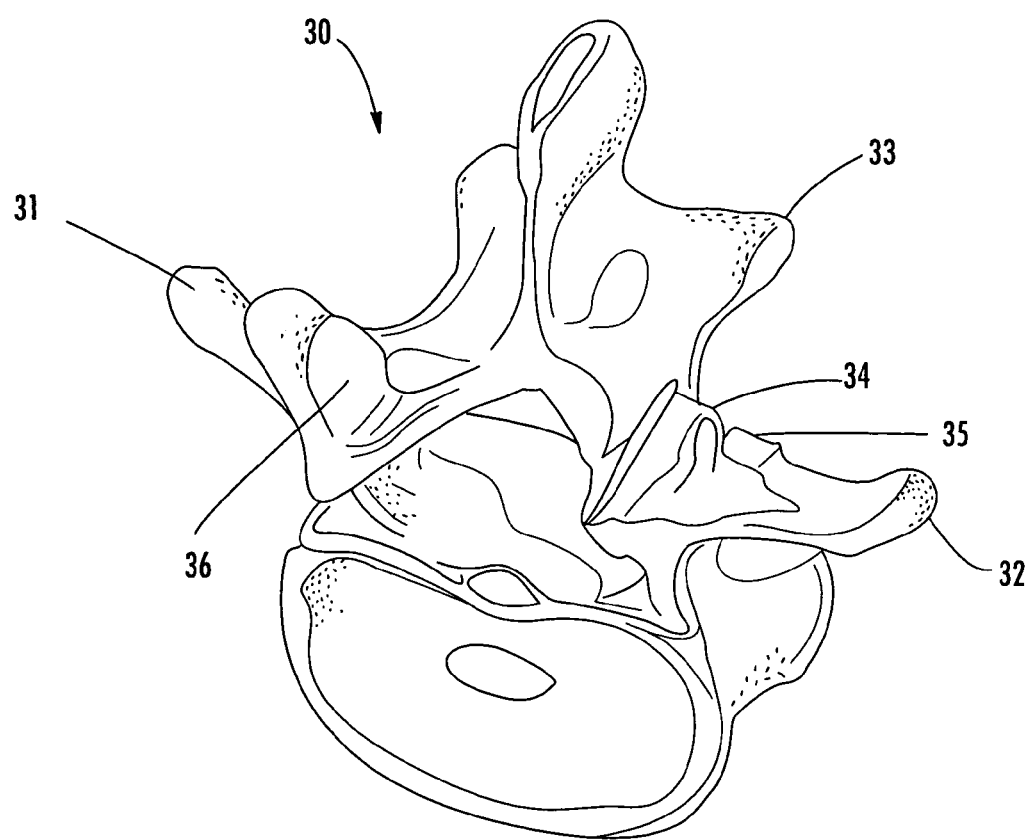
FIG. 3 is a diagram illustrating a vertebra.

FIG. 3 shows a vertebra 30 of the lumbar region of a human spine. The vertebra 30 includes a transverse process 32, the inferior articular process 33, the mamillary process 34, the accessory process 35 and the superior articular process 36. The vertebra 30 includes each of the foregoing structures on both sides of it as shown, for example as second transverse process 31 on the other side of vertebra 30.

Figure 1:
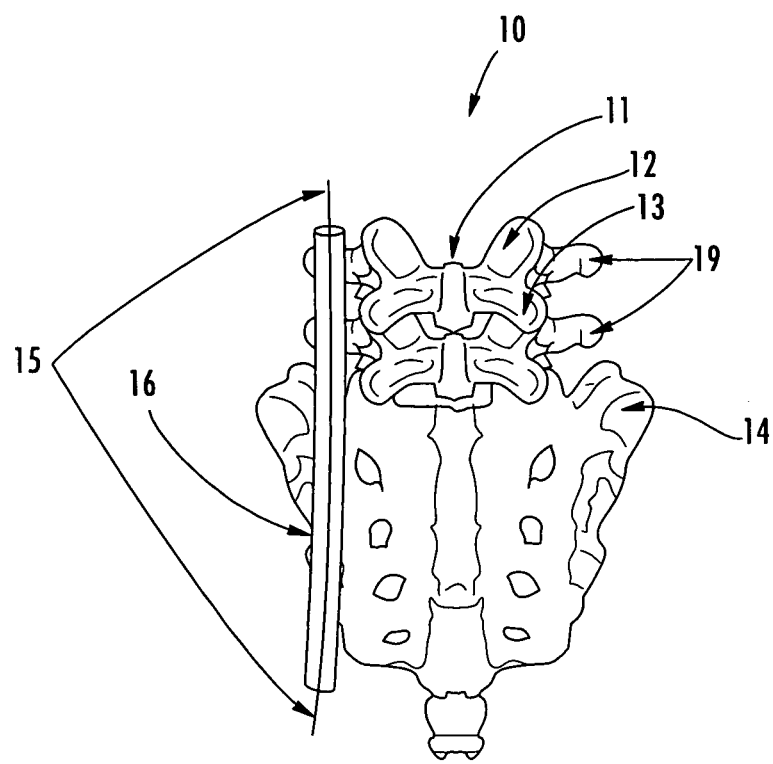
FIG. 1 is a schematic diagram illustrating a dilator in relation to transverse processes of two vertebrae according to an aspect of the present invention.
Figure 2:
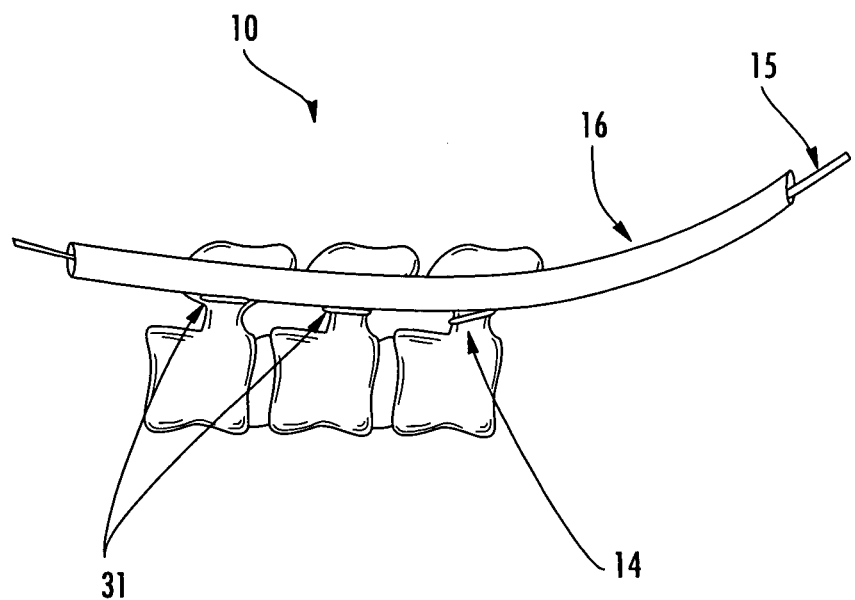
FIG. 2 is a schematic diagram illustrating a dilator in relation to transverse processes of two vertebrae according to an aspect of the present invention.

FIG. 1 shows a portion of the lumbar spine showing two vertebra and the ala 14. Each of the vertebrae includes the spinous process 11, the lamina 12, and the pars 13. According to the invention, a guide 15, such as a wire guide, is shown and a dilator 16 is shown threaded or placed over the guide 15.

Figure 4:
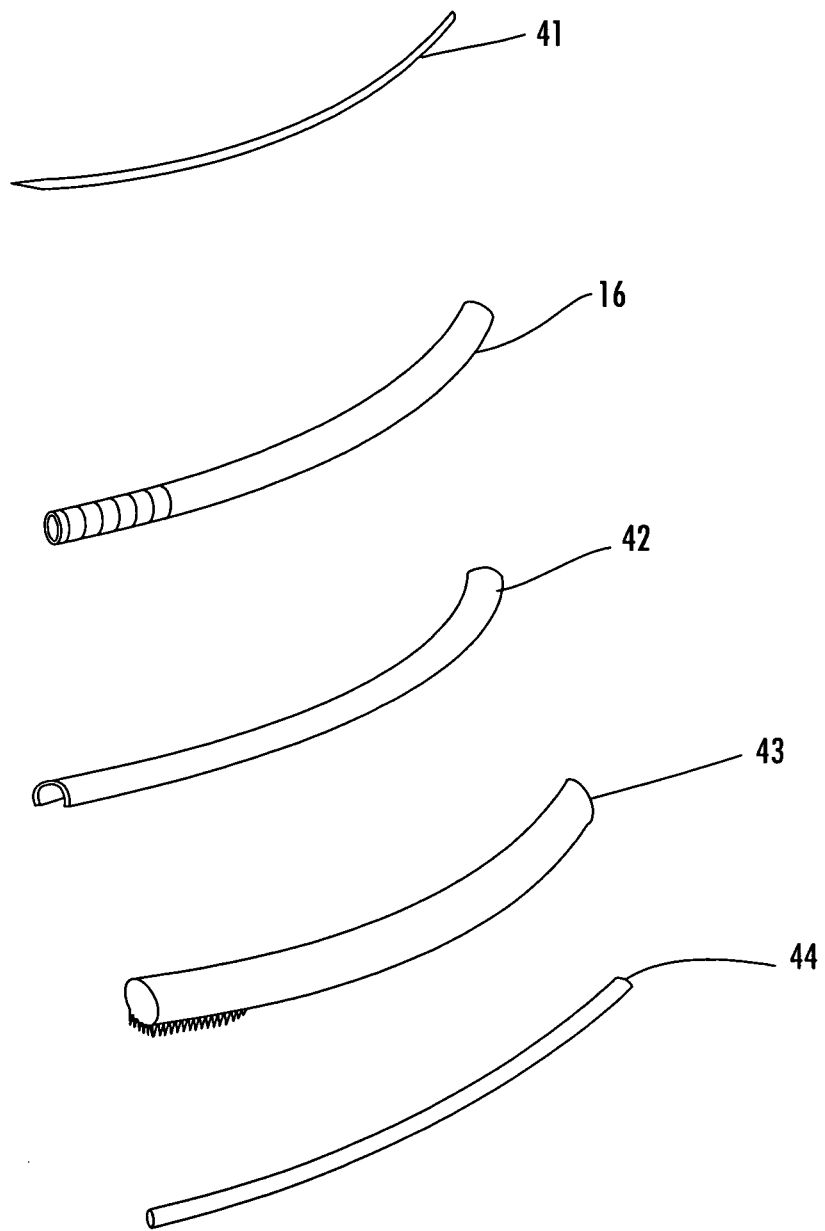
FIG. 4 illustrates instruments that may be used in a procedure according to an aspect of the present invention.

FIG. 4 shows the preferred medical instruments that may be used in a procedure according to the methodology of the present invention. A trocar 41 has a sharp tip and is typically a solid object like a rod. Preferably it is curved. The trocar 41 may be embodied as part of a cannula, such as a cannular trocar. Dilator 16 is typically used to create a wider channel than the one made by the trocar 41. Dilator 16 typically has a hollow center so that it slides over the in-place trocar. Then the guide wire or trocar is removed. Delivery tube 42, sometimes also referred to as a carrier tube, is also typically hollow and allows other instruments, such as endoscopes to facilitate viewing the condition of tissue or the like, a decorticator, a rasp, a pushing instrument, a syringe, medication, or other substances, to be delivered to the region of interest, or to remove tissue, bone, or specimen from the region of interest. A rasp 43 is typically solid, and typically has a serrated surface or distal edge. Pusher 44 is generally solid, or at least its useful end includes a forward directed solid surface. It is used to push medication, a liquid or other substance, such as a bone matrix or bone fusion substance to the region of interest.

A procedure according to an aspect of the present invention will now be described with reference to FIGS. 1 and 4. It will be understood however, that various steps outlined herein may be omitted or combined with other steps, and that the order of the steps outlined herein may not be essential to the spirit of the invention. Further, other steps or procedures may be necessary for any given medical procedure. For example, a local anesthetic may be first applied to anesthetize the patient for the duration of the procedure. When using an autograft bone graft, bone marrow aspirate may have to be first extracted from the patient, such as from the iliac crest using a syringe. When using allograft bone graft, bone matrix may have to be prepared in advance of the procedure.

An endoscope may be inserted via the delivery tube 42 or via a channel created through another incision to get a better view of the region of interest or of related conditions. According to an embodiment of the present invention, a lateral fluoroscope may be used to get substantially real-time views of the region of interest. Fluoroscopes may provide an interior-posterolateral view and a lateral view of the lumbar spine or the region of interest. Moreover, while spinal fusion with respect to the lumbar region of the spine is discussed for illustrative purposes throughout herein, it will be understood that the inventive procedure may also be used for other areas of the spine.

According to an aspect of the invention, the curvature of a relevant area of the spine may first have to be determined in order to determine the proper curvature for the medical instruments, such as the trocar guide and/or the dilator 16. The medical instruments could be malleable and bent by the physician to the appropriate curve, or several sets of such instruments pre-adjusted or pre-curved could be provided to accommodate different spine curvatures.

An incision is first made in the body after suitable anesthetic take "hold" and the trocar 41 is inserted to create access to the vertebrae of interest. Then, the dilator 16 is inserted over the trocar 41 and a suitable channel is developed. The trocar is then removed. The delivery tube 42, preferably u-shaped in cross-section, is inserted or threaded over the dilator 16. With the delivery tube in place, the dilator 16 can then be removed by removing it through the delivery tube 42.

A rasp 43 or other type of decorticator is then used to remove a portion of the cortex of the vertebrae in question. It is threaded through the open end of the delivery tube and the distal working end extends downwardly or outwardly from the delivery tube, i.e., through its open channel along its bottom or through its distal open end. In spinal fusion at the transverse process, portions of the transverse process on both sides of the spine would typically be decorticated. This decortication process would be performed for each vertebra to be fused. For example, as shown in FIG. 1, the transverse processes 19 of the two vertebra shown will be decorticated on both sides of each vertebra to expose a bed for the spinal fusion. Also, the ala 14 could be additionally roughened/decorticated by rasp 43. After use, the rasp 43 is removed from the delivery tube 42 by pulling it out, along the longitudinal axis of the delivery tube.

The bone fusion substance, such as morselized bone and/or bone morphogenic protein (BMP), is then applied to the decorticated site via the delivery tube 42 to connect the decorticated areas of the adjacent vertebrae on each side of the spine. The bone fusion substance may also include bone marrow aspirate, such as bone marrow aspirate previously taken from the iliac crest, cadaver bone marrow, processed bone marrow from other species, synthesized material, or some combination of the foregoing. For example, as shown in FIG. 1, the decorticated areas of the transverse processes 19 on the right side of the spine of adjacent vertebrae are fused using the bone fusion substance, and the transverse processes of the left side of the spine are also fused using the bone fusion substance.

The bone fusion substance is applied via a pusher 44 that is inserted into the delivery tube 42 after the rasp has been removed. The front end of the pusher advances the material to the site. The pusher is shaped and sized to fit and glide within the delivery tube, similar to the rasp. Also, after the bone fusion substance is delivered, the delivery tube 42 may be removed while the pusher 44 may continue to be held in place to control the bone fusion substance or to urge or direct the bone fusion substance to its intended location or to its intended shape. The pusher 44 is then removed and the delivery tube, if not previously removed, is then removed.

The foregoing description is not intended to limit the scope of the invention.

What is claimed is:

1. A system of medical instruments for performing a spine fusion procedure on a region of a human patient, the system comprising:
 a trocar adapted to be inserted into the human patient through an incision to thereby establish a path from the outside of a body to a spine fusion region of interest, said trocar being at least of length to extend to two or more processes and vertically stacked vertebrae of the human patient;
 a hollow dilator, of length to extend to the two or more processes and vertically stacked vertebrae of the human patient and adapted to be inserted over said trocar to provide a larger bore from a point outside of the human patient to the spine fusion region of interest;

a longitudinally extending delivery tube being u-shaped in cross-section and having an outside surface, a lumen defined therethrough and a side slit extending over its entire length, said side slit emerging at the outside surface of said delivery tube, said delivery tube being adapted to be inserted over said dilator after which said delivery tube is adapted to allow said dilator and said trocar to then be removed, said delivery tube being of length to extend to the two or more processes and vertically stacked vertebrae of the human patient;

a decorticator having a longitudinal axis and capable for receipt and slidable movement within said lumen of said delivery tube and provided with a working end having a decorticating surface extending out and through said slit and capable of decorticating at multiple locations along a length of said slit, the decorticating surface provided with a filing surface and dimensioned and adapted to be inserted into said delivery tube with said working end projecting through said side slit to decorticate a transverse process region; and a pusher instrument also suitably dimensioned and adapted to be inserted into said delivery tube after removal of said decorticator to push a bone fusion substance to the region.

2. The system of medical instruments as claimed in claim 1, wherein said trocar, said dilator, said delivery tube, said decorticator and said pusher instrument are selectively malleable to a curvature of at least a portion of a human spine according to a spine curvature of the human patient for the region.

3. The system of medical instruments as claimed in claim 1, wherein curvatures of said trocar, said dilator, said delivery tube, said decorticator, and said pusher instrument are curved to correspond to a curvature of at least a portion of a human spine.

* * * * *